US010925483B2

United States Patent
Nozawa et al.

(10) Patent No.: US 10,925,483 B2
(45) Date of Patent: Feb. 23, 2021

(54) OPTICAL COHERENCE TOMOGRAPHIC DEVICE AND LIGHT SOURCE

(71) Applicant: Tomey Corporation, Nagoya (JP)

(72) Inventors: Yuji Nozawa, Nagoya (JP); Chihiro Kato, Nagoya (JP); Takashi Kamo, Nagoya (JP)

(73) Assignee: TOMEY CORPORATION, Nagoya (JP)

( * ) Notice: Subject to any disclaimer, the term of this patent is extended or adjusted under 35 U.S.C. 154(b) by 37 days.

(21) Appl. No.: 16/217,189

(22) Filed: Dec. 12, 2018

(65) Prior Publication Data
US 2019/0191991 A1  Jun. 27, 2019

(30) Foreign Application Priority Data

Dec. 22, 2017  (JP) .............................. JP2017-246663

(51) Int. Cl.
*A61B 3/10* (2006.01)
*A61B 3/00* (2006.01)

(52) U.S. Cl.
CPC ............ *A61B 3/102* (2013.01); *A61B 3/0008* (2013.01)

(58) Field of Classification Search
CPC ..... A61B 3/102; A61B 3/0008; A61B 5/0066; G01B 9/02091
See application file for complete search history.

(56) References Cited

U.S. PATENT DOCUMENTS

| 8,390,818 | B2 | 3/2013 | Hirose et al. |
| 9,131,841 | B2 | 9/2015 | Hirose |
| 2011/0255054 | A1 | 10/2011 | Hacker et al. |
| 2012/0147326 | A1* | 6/2012 | Yatagai ................. A61B 3/102 |
| | | | 351/206 |
| 2016/0317028 | A1 | 11/2016 | Murata et al. |
| 2017/0311797 | A1* | 11/2017 | Kuo ..................... A61B 3/1233 |
| 2018/0012359 | A1* | 1/2018 | Prentasic ............. G06T 7/0014 |
| 2018/0084993 | A1 | 3/2018 | Buckland et al. |

FOREIGN PATENT DOCUMENTS

| JP | 5306041 B2 | 10/2013 |
| JP | 5721779 B2 | 5/2015 |
| JP | 2016-523613 A | 8/2016 |
| JP | 2017-176842 A | 10/2017 |
| WO | 2014/197553 A2 | 12/2014 |

* cited by examiner

*Primary Examiner* — Jonathan M Hansen
(74) *Attorney, Agent, or Firm* — Shumaker, Loop & Kendrick, LLP

(57) ABSTRACT

An optical coherence tomographic device configured to acquire a tomographic image of a subjected eye is disclosed herein. The optical coherence tomographic device may include a light source of wavelength sweeping type; and a measurement optical system configured to irradiate the subjected eye with light outputted from the light source, where $D/S \times \lambda > 1.61$ may be satisfied, with a diameter of the light outputted from the light source at an incident position to the subjected eye is D, a wavelength swept frequency of the light source is S, and a center wavelength of the light outputted from the light source is $\lambda$.

7 Claims, 5 Drawing Sheets

OPTICAL COHERENCE TOMOGRAPHIC DEVICE AND LIGHT SOURCE

CROSS-REFERENCE

This application claims priority to Japanese Patent Application No. 2017-246663, filed on Dec. 22, 2017, the entire contents of which are incorporated herein by reference.

TECHNICAL FIELD

The technique disclosed herein relates to an optical coherence tomographic device and a light source used for the same.

BACKGROUND ART

Optical coherence tomographic devices configured to measure an axial length of a subjected eye and positions of parts in the subjected eye have been developed. For example, an optical coherence tomographic device of Japanese Patent Application Publication No. 2017-176842 is provided with a measurement optical system configured to irradiate a subjected eye with light outputted from a light source and guide reflected light from the subjected eye, and a reference optical system configured to irradiate a reference surface with the light outputted from the light source and guide reflected light from the reference surface. In measurement, a position of a target part in the subjected eye is specified from interference light in which the reflected light guided by the measurement optical system is combined with the reflected light guided by the reference optical system.

SUMMARY

In an optical coherence tomographic device, such as the optical coherence tomographic device of Japanese Patent Application Publication No. 2017-176842, a subjected eye is normally irradiated with light having a relatively small diameter of 1 to 2 mm. However, if a crystalline lens of the subjected eye has an opacified portion, for example, due to cataract, the light outputted from a light source to the subjected eye may attenuate at the opacified portion, and an amount of light reaching a retina may become small. As a result, it has been problematic that detection of reflected light from the retina is difficult and thus measurement for a position of the retina, an axial length and the like is difficult. In view of this, the disclosure herein discloses a technique capable of increasing a signal strength of reflected light from a retina of a subjected eye.

An optical coherence tomographic device disclosed herein may be configured to acquire a tomographic image of a subjected eye. The optical coherence tomographic device may comprise a light source of wavelength sweeping type; and a measurement optical system configured to irradiate the subjected eye with light outputted from the light source. $D/S \times \lambda > 1.61$ may be satisfied, with a diameter of the light outputted from the light source at an incident position to the subjected eye is D, a wavelength swept frequency of the light source is S, and a center wavelength of the light outputted from the light source is $\lambda$.

In the above optical coherence tomographic device, signal reception sensitivity can be increased by irradiating the subjected eye with light that satisfies the above-mentioned condition. Due to this, a signal of reflected light from a retina can be obtained with high sensitivity.

A light source disclosed herein may be of wavelength sweeping type, may be equipped in an optical coherence tomographic device configured to acquire a tomographic image of a subjected eye and may be configured to output light with which the subjected eye is irradiated. With a diameter of light outputted from the light source at an incident position to the subjected eye is D, a wavelength swept frequency is S, and a center wavelength is $\lambda$, the light source may be configured to be capable of adjusting at least one of the wavelength swept frequency S and the center wavelength $\lambda$ so that $D/S \times \lambda > 1.61$ is satisfied.

The above light source can adjust at least one of the wavelength swept frequency S and the center wavelength $\lambda$ so as to irradiate the subjected eye with light that satisfies the above-mentioned condition. Due to this, the light source can bring similar operation and effect to those of the above optical coherence tomographic device.

Another optical coherence tomographic device disclosed herein may be configured to acquire a tomographic image of a subjected eye. The optical coherence tomographic device may comprise a light source of wavelength sweeping type; and a measurement optical system configured to irradiate the subjected eye with light outputted from the light source. A diameter D of the light outputted from the light source at an incident position to the subjected eye may be 3 mm or more.

In the other optical coherence tomographic device above, an amount of light reaching a retina can be increased since the diameter D of the light outputted from the light source at the incident position to the subjected eye is 3 mm or more. Due to this, even when a crystalline lens of the subjected eye has an opacified portion, a signal of reflected light from the retina can be obtained.

DETAILED DESCRIPTION

Figure 1:
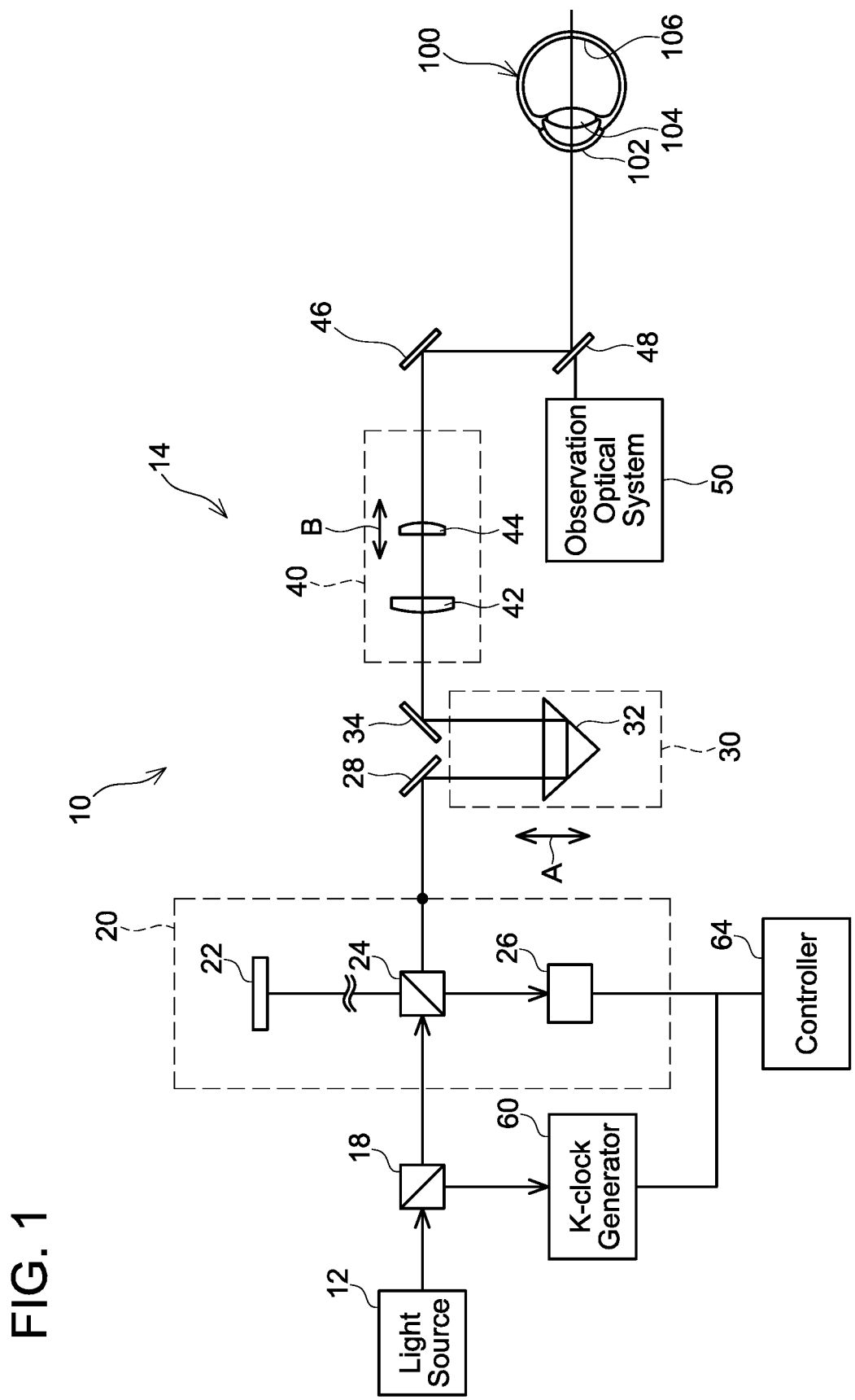
FIG. 1 is a diagram showing a schematic configuration of an optical system of an optical coherence tomographic device of an embodiment.

Representative, non-limiting examples of the present invention will now be described in further detail with reference to the attached drawings. This detailed description is merely intended to teach a person of skill in the art further details for practicing preferred aspects of the present teachings and is not intended to limit the scope of the invention. Furthermore, each of the additional features and teachings disclosed below may be utilized separately or in conjunction with other features and teachings to provide improved optical coherence tomographic devices and light sources, as well as methods for using and manufacturing the same.

Moreover, combinations of features and steps disclosed in the following detailed description may not be necessary to practice the invention in the broadest sense, and are instead taught merely to particularly describe representative examples of the invention. Furthermore, various features of the above-described and below-described representative examples, as well as the various independent and dependent claims, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

Some of the features characteristic to below-described embodiments will herein be listed. It should be noted that the respective technical elements are independent of one another, and are useful solely or in combinations. The combinations thereof are not limited to those described in the claims as originally filed.

(Feature 1) In an optical coherence tomographic device disclosed herein, a diameter D may be 3 mm or more.

(Feature 2) In the optical coherence tomographic device disclosed herein, a wavelength swept frequency S may be 10 Hz or more and 5000 Hz or less. According to such a configuration, signal reception sensitivity can be further improved, and occurrence of artifacts can be suppressed.

(Feature 3) In the optical coherence tomographic device disclosed herein, a center wavelength λ may be 700 nm or more and 1400 nm or less. According to such a configuration, intensity of light can be suppressed from attenuating while the light propagates within an eye, and the signal reception sensitivity can be further improved.

(Feature 4) The optical coherence tomographic device disclosed herein may further comprise a controller configured to control the light source. The light source may be configured to be capable of adjusting at least one of the wavelength swept frequency S and the center wavelength λ. The controller may be configured to adjust at least one of the wavelength swept frequency S and the center wavelength λ of the light outputted from the light source. According to such a configuration, $D/S \times \lambda > 1.61$ can be easily satisfied by adjusting at least one of the wavelength swept frequency S and the center wavelength λ of the light outputted from the light source according to the diameter D of the light outputted from the light source at an incident position to a subjected eye.

(Feature 5) In the optical coherence tomographic device disclosed herein, a measurement optical system may be configured to be capable of adjusting the diameter D of the light outputted from the light source at the incident position to the subjected eye. The measurement optical system may be configured to adjust the diameter D so that the diameter D becomes equal to or less than a pupil diameter of the subjected eye. According to such a configuration, the diameter D of the light at the incident position to the subjected eye can be adjusted according to the pupil diameter of the subjected eye. Due to this, the subjected eye can be irradiated efficiently with the light.

(Feature 6) In the optical coherence tomographic device disclosed herein, the measurement optical system may comprise a focal point adjuster configured to be capable of adjusting a focal position of the light outputted from the light source. According to such a configuration, the diameter D can be easily adjusted by using the focal point adjuster.

The optical coherence tomographic device disclosed herein may further comprise a light receiving element configured to receive reflected light from the subjected eye and to output a signal which corresponds to an intensity of the reflected light; a sampling circuit configured to sample the signal outputted from the light receiving element; and a sample clock generator configured to generate a clock signal which defines a timing for sampling the signal based on a frequency of the light outputted from the light source. According to such a configuration, distortion in the sampled signal can be suppressed, and a tomographic image with higher resolution can be obtained.

Embodiment

An optical coherence tomographic device of an embodiment will be described hereinbelow. As shown in FIG. 1, the optical coherence tomographic device comprises a light source 12, a measurement unit 10 configured to examine a subjected eye 100, and a K-clock generator 60. Light outputted from the light source 12 enters a beam splitter 18 and is split into light to be guided to the measurement unit 10 and light to be guided to the K-clock generator 60 in the beam splitter 18.

The measurement unit 10 comprises an interference optical system 14 configured to cause reference light interfere with reflected light that is reflected from the subjected eye 100, an observation optical system 50 configured to observe an anterior part of the eye 100, and an alignment optical system (not shown) configured to align the measurement unit 10 with respect to the subjected eye 100 in a predetermined positional relationship. An alignment optical system that has been used in a well-known optical coherence tomographic device can be used as the aforementioned alignment optical system, and thus detailed explanation thereof is herein omitted.

The interference optical system 14 is constituted of a measurement optical system configured to irradiate the subjected eye 100 with light from the light source 12 and guide reflected light therefrom, a reference optical system configured to irradiate a reference surface with light from the light source 12 and guide reflected light therefrom, and a light receiving element 26 configured to receive interference light in which the reflected light guided by the measurement optical system is combined with the reflected light guided by the reference optical system.

The light source 12 is of wavelength sweeping type, and a wavelength of light outputted therefrom changes with a predetermined period. When the wavelength of the light outputted from the light source 12 changes, a reflection position of reflected light, among reflected lights from respective parts of the subjected eye 100 in its depth direction, that causes interference with the reference light changes correspondingly to the wavelength of the outputted light. This change in the reflection position takes place in the depth direction of the subjected eye 100. Therefore, positions of the respective parts (that is, a crystalline lens 104, a retina 106 and the like) inside the subjected eye 100 can be specified by measuring the interference light while changing the wavelength of the outputted light.

The light source 12 may be configured to output light having a wavelength (specifically, a center wavelength) of 700 nm or more and 1400 nm or less. Light having a wavelength of less than 700 nm is visible. Therefore, by outputting the light having the wavelength of 700 nm or more, a subject does not have to be dazzled and a pupil of the subjected eye 100 can be suppressed from constricting. Further, light having a wavelength of more than 1400 nm is likely to be absorbed by water. Therefore, by outputting the light having the wavelength of 1400 nm or less, intensity of the light can be suppressed from attenuating while the light propagates within the eye, and detection sensitivity for light received by the light receiving element 26 can be suppressed from decreasing. In the present embodiment, the light source 12 outputs light having a wavelength of 700 nm. Further, a wavelength swept frequency of the light source 12 may be 10 Hz or more and 5000 Hz or less. With a low wavelength swept frequency, the detection sensitivity for light received by the light receiving element 26 is improved. Therefore, by setting the wavelength swept frequency to 5000 Hz or less, the light receiving element 26 can detect the interference light favorably. Further, if the subjected eye 100 moves while a tomographic image thereof is captured, artifacts are caused in the captured tomographic image. One of causes for the subjected eye 100 to move during image capturing is oscillation due to heartbeats (1 to 2 Hz) of the subject. Therefore, by setting the wavelength swept frequency to 10 Hz or more, the wavelength swept frequency becomes faster than the heartbeats of the subject. Thereby, the subjected eye 100 can be suppressed from moving due to the heartbeats of the subject during image capturing, and artifacts in a captured tomographic image can be suppressed from occurring. In the present embodiment, the wavelength swept frequency of the light source 12 is 1300 Hz. The wavelength swept frequency of light outputted from the light source 12 can be adjusted by a controller 64, of which configuration will be described later.

The measurement optical system is constituted of a beam splitter 24, a mirror 28, a 0-point (zero-point) adjustment mechanism 30, a mirror 34, a focal point adjustment mechanism 40 (focal point adjuster 40), a mirror 46, and a hot mirror 48. Light outputted from the light source 12 is guided to the measurement unit 10 through the beam splitter 18. The light guided to the measurement unit 10 enters the subjected eye 100 through the beam splitter 24, the mirror 28, the 0-point adjustment mechanism 30, the mirror 34, the focal adjustment mechanism 40, the mirror 46, and the hot mirror 48. Reflected light from the subjected eye 100 is guided to the light receiving element 26 through the hot mirror 48, the mirror 46, the focal point adjustment mechanism 40, the mirror 34, the 0-point adjustment mechanism 30, the mirror 28, and the beam splitter 24. The 0-point adjustment mechanism 30 and the focal point adjustment mechanism 40 will be described in detail later.

The reference optical system is constituted of the beam splitter 24 and a reference mirror 22. A part of the light guided to the measurement unit 10 through the beam splitter 18 is reflected by the beam splitter 24, is directed to the reference mirror 22, and then is reflected by the reference mirror 22. The light reflected by the reference mirror 22 is guided to the light receiving element 26 through the beam splitter 24. The reference mirror 22, the beam splitter 24, and the light receiving element 26 are disposed in an interferometer 20, and their positions are fixed. Therefore, in the optical coherence tomographic device of the present embodiment, a reference optical path length is constant and does not change.

The light receiving element 26 detects the interference light in which the light guided by the reference optical system is combined with the light guided by the measurement optical system. For example, a photodiode can be used as the light receiving element 26.

The observation optical system 50 irradiates the subjected eye 100 with observation light through the hot mirror 48 and captures reflected light that is reflected from the subjected eye 100 (that is, reflected light of the observation light). Here, the hot mirror 48 reflects the light from the light source 12 of the interference optical system 14 and transmits light from a light source of the observation optical system 50. As a result, in the optical coherence tomographic device of the present embodiment, it is possible to perform the measurement by the interference optical system 14 and the observation of the anterior part of the eye by the observation optical system 50 at the same time. An observation optical system that has been used in a well-known optical coherence tomographic device can be used as the observation optical system 50. For this reason, detailed configuration thereof is not explained herein.

Figure 2:
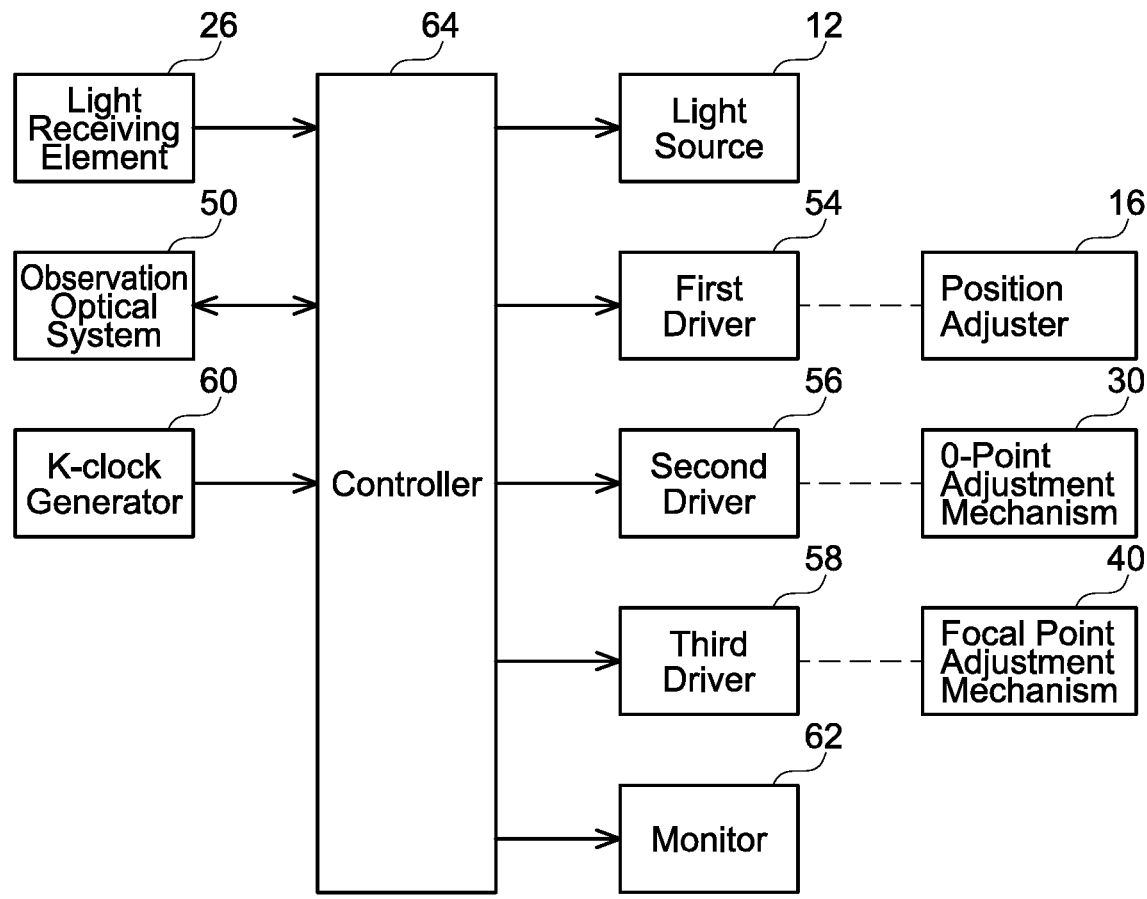
FIG. 2 is a block diagram showing a control system of the optical coherence tomographic device of the embodiment.
Figure 3:
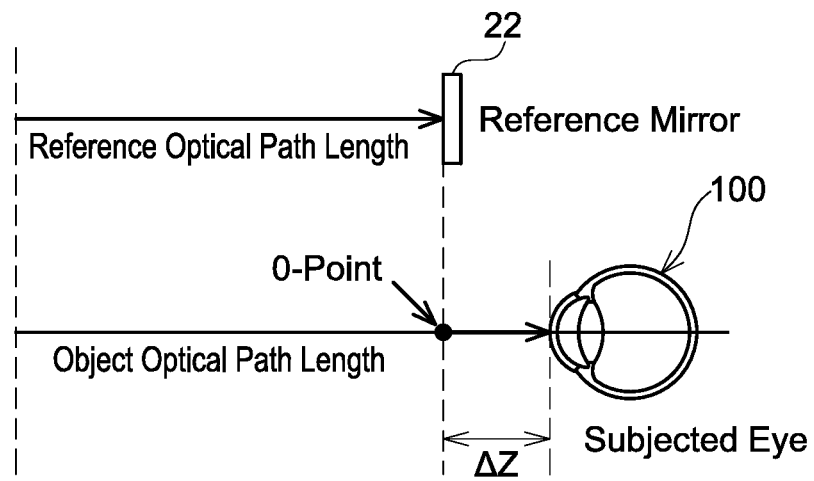
FIG. 3 is a diagram for explaining a function of a 0-point adjustment mechanism.

The 0-point adjustment mechanism 30 and the focal point adjustment mechanism 40 provided in the measurement optical system will be explained below. The 0-point adjustment mechanism 30 is provided with a corner cube 32, and a second driver 56 (shown in FIG. 2) configured to move the corner cube 32 back and forth with respect to the mirrors 28 and 34. When the second driver 56 moves the corner cube 32 in a direction of an arrow A in FIG. 1, an optical path length from the light source 12 to the subjected eye 100 (that is, an object optical path length of the measurement optical system) changes. As shown in FIG. 3, when there is an optical path difference ΔZ between the object optical path length from the light source 12 to a detection surface (a corneal surface in FIG. 3) of the subjected eye 100 (more specifically, the light source 12 to the detection surface plus the detection surface to the light receiving element 26) and the reference optical path length from the light source 12 to the reference mirror 22 (more specifically, the light source 12 to the reference mirror 22 plus the reference mirror 22 to the light receiving element 26), the larger the optical path difference ΔZ becomes, the lower intensity of the interference light between reflected light that is reflected from the detection surface and the reference light becomes. Conversely, the smaller the optical path difference ΔZ becomes, the higher the intensity of the interference light becomes. Therefore, in the present embodiment, by changing the object optical path length with the 0-point adjustment mechanism 30, it is possible to change a position at which the reference optical path length and the object optical path length match (that is, the 0-point) from the surface of a cornea 102 to a surface of the retina 106.

The focal point adjustment mechanism 40 is provided with a convex lens 42 disposed on a light source 12 side, a convex lens 44 disposed on a subjected eye 100 side, and a third driver 58 (shown in FIG. 2) configured to move the convex lens 44 back and forth with respect to the convex lens 42 in an optical axis direction. The convex lens 42 and the convex lens 44 are disposed on the optical axis and change a position of a focal point of incident parallel light. Thus, when the third driver 58 drives the convex lens 44 in a direction of an arrow B in FIG. 1, a position of the focal point of incident light to the subjected eye 100 changes in the depth direction of the subjected eye 100.

Figure 4A:
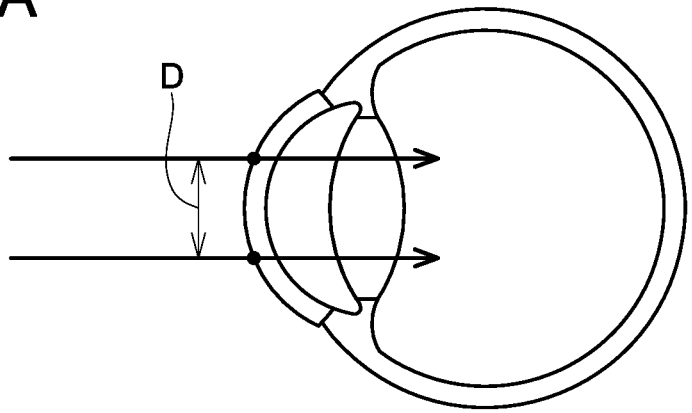
FIGS. 4A, 4B, and 4C show diagrams for explaining a function to change a diameter of incident light to a subjected eye by a focal point adjustment mechanism.
Figure 4B:
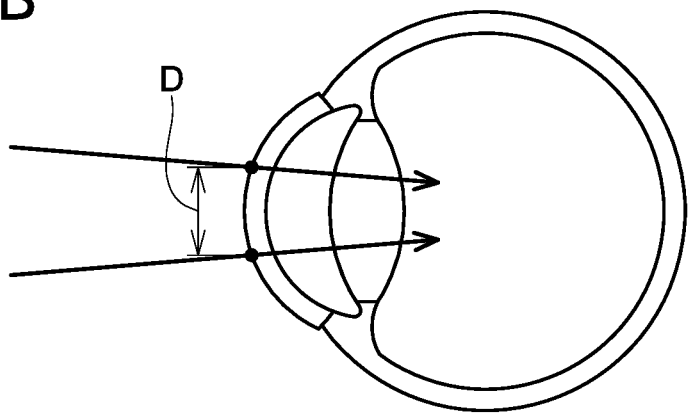
Figure 4C:
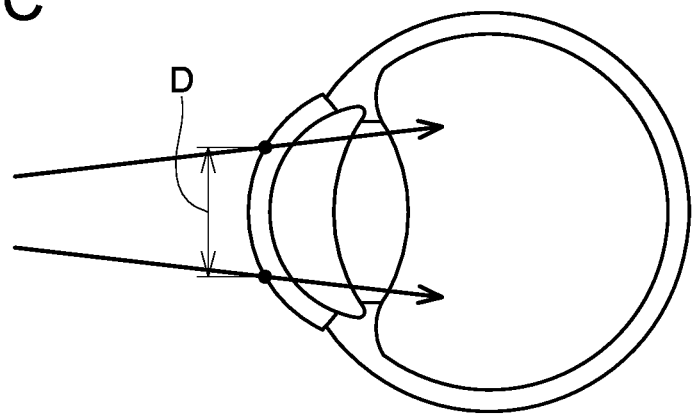

By adjusting an interval between the convex lens 42 and the convex lens 44 in the focal point adjustment mechanism 40, a diameter D of light at an incident position to the subjected eye 100 (that is, at a position on a front surface of the cornea 102) (hereinbelow, may simply be referred to as "diameter D of light") can be changed. Specifically, when the interval between the convex lens 42 and the convex lens 44 is adjusted such that light from the convex lens 44 becomes parallel light, the parallel light enters the subjected eye 100 as shown in FIG. 4A. Meanwhile, when the convex lens 44 is moved away from the convex lens 42 in the state of FIG. 4A, the light from the convex lens 44 becomes convergent light and the convergent light enters the subjected eye 100 as shown in FIG. 4B. In this case, the diameter D of the convergent light entering the subjected eye 100 is smaller than the diameter D of the parallel light entering the subjected eye 100 (that is, the diameter D in FIG. 4A). Further, when the convex lens 44 is moved closer to the convex lens 42 in the state of FIG. 4A, the light from the convex lens 44 becomes diverging light and the diverging light enters the subjected eye 100 as shown in FIG. 4C. In this case, the diameter D of the diverging light entering the subjected eye 100 is larger than the diameter D of the parallel light entering the subjected eye 100 (that is, the diameter D in FIG. 4A). As above, by changing the diameter D of light, a diameter of light entering the subjected eye 100 can be changed.

Figure 5A:
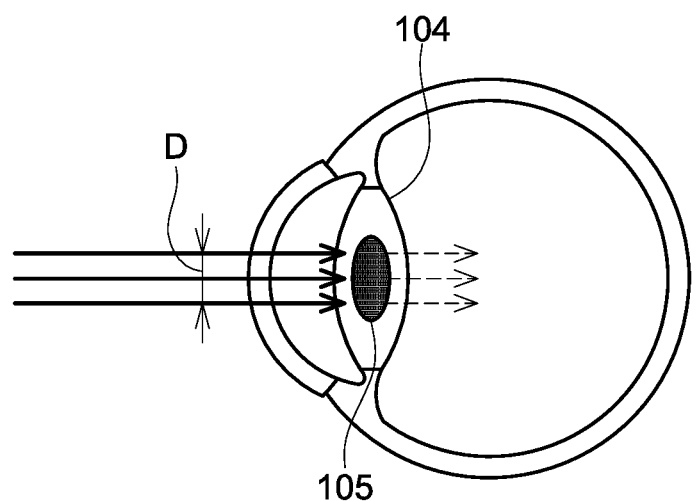
FIGS. 5A and 5B show diagrams schematically showing incident light to a subjected eye with its crystalline lens having an opacified portion with 5A showing a case with a small diameter of light and 5B showing a case with a large diameter of light.
Figure 5B:
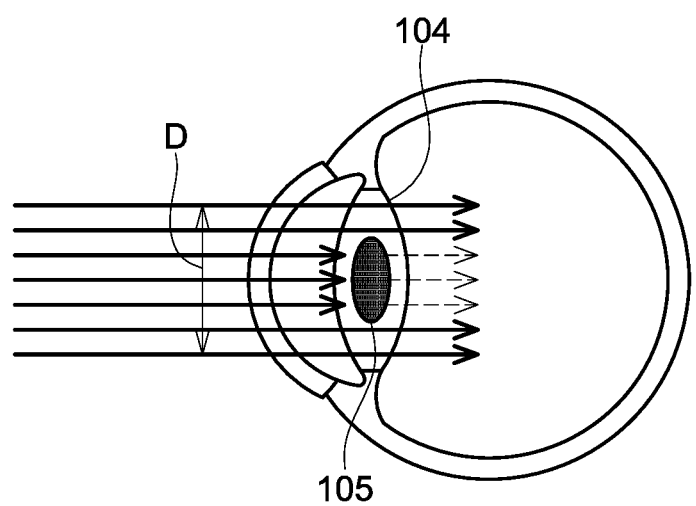

There may be a case where the crystalline lens 104 of the subjected eye 100 has an opacified portion 105 due to cataract, for example. FIGS. 5A, 5B schematically show light entering the subjected eye 100 in the case where the crystalline lens 104 of the subjected eye 100 has the opacified portion 105. For simpler explanation, FIGS. 5A, 5B show the light entering the subjected eye 100 as parallel light, regardless of magnitude of the diameter D of light. As shown in FIG. 5A, when the diameter D of light is small, the light outputted from the light source 12 attenuates at the opacified portion 105, by which an amount of light reaching the retina 106 becomes small. On the other hand, when the diameter D of light is large as shown in FIG. 5B, a part of the light entering the subjected eye 100 attenuates at the opacified portion 105, while rest of the light entering the subjected eye 100 reaches the retina 106 without passing the opacified portion 105. Due to this, even with the subjected eye 100 having the crystalline lens 104 with the opacified portion 105, a signal strength of reflected light from the retina 106 can be increased by making the diameter D of light entering the subjected eye 100 large. The diameter D of light may be 3 mm or more and equal to a pupil diameter of the subjected eye 100 or less. With the diameter D of light of 3 mm or more, the light can easily reach the retina 106. Further, with the diameter D of light equal to the pupil diameter of the subjected eye 100 or less, the light can enter inside of the eye efficiently. When a measurement is performed, the pupil diameter of the subjected eye 100 may be increased by a mydriatic agent and the like. By increasing the pupil diameter of the subjected eye 100, the diameter D of light can be increased.

The K-clock generator 60 optically generates a sample clock (K-clock) signal from the light split through the beam splitter 18 to sample an interference signal at equal-interval frequencies (at uniform frequency intervals with respect to light frequency). The generated K-clock signal is outputted to the controller 64. Due to this, distortion in the interference signal can be suppressed, and deterioration in resolution can be prevented.

Further, the optical coherence tomographic device of the present embodiment is provided with a position adjuster 16 (shown in FIG. 2) configured to adjust a position of the measurement unit 10 (specifically, the optical system in the measurement unit 10 excluding the interferometer 20) with respect to the subjected eye 100, and a first driver 54 (shown in FIG. 2) configured to drive the position adjuster 16. A position adjustment process by the position adjuster 16 will be described later.

Next, a configuration of a control system of the optical coherence tomographic device of the present embodiment will be described. As shown in FIG. 2, the optical coherence tomographic device is controlled by the controller 64. The controller 64 is constituted of a microcomputer (a microprocessor) including a CPU, a ROM, a RAM, and the like. The light source 12, the first to third drives 54 to 58, a monitor 62, and the observation optical system 50 are connected to the controller 64. The controller 64 controls on/off of the light source 12 and also controls the wavelength swept frequency of light outputted from the light source 12. Therefore, the controller 64 can change the wavelength swept frequency of light outputted from the light source 12. Further, the controller 64 drives respective mechanisms 16, 30, and 40 by controlling the first to third drives 54 to 58, and displays on the monitor 62 an image of the anterior part of the eye captured in the observation optical system 50 by controlling the observation optical system 50.

As described above, the controller 64 is configured to adjust the wavelength swept frequency of the light outputted from the light source 12, and is configured to adjust the diameter D of light entering the subjected eye 100 by driving the third driver 58 to drive the focal adjustment mechanism 40. Thus, the controller 64 can adjust a wavelength swept frequency S of light outputted from the light source 12 and the diameter D of light entering the subjected eye 100, such that $D/S \times \lambda > 1.61$ is satisfied. In this conditional expression, S indicates a wavelength swept frequency and $\lambda$ indicates a wavelength of light. When the diameter D of light is increased to satisfy $D/S \times \lambda > 1.61$, the amount of light reaching the retina 106 can be increased. Further, when the wavelength swept frequency S is decreased to satisfy $D/S \times \lambda > 1.61$, the detection sensitivity for light received by the light receiving element 26 is improved. Conventionally, the subjected eye 100 had been measured with high wavelength swept frequency S to enhance processing capacity. However, as a result of researches by the inventor of the technique disclosed herein in a perspective of obtaining favorable tomographic images even with the subjected eye 100 having the crystalline lens 104 with the opacified portion 105, it has been revealed that a relationship between the diameter D of light, the wave swept frequency S, and the wavelength $\lambda$ affects the measurement. Then, as a result of further research by the inventor on the relationship between the diameter D of light, the wave swept frequency S, and the wavelength $\lambda$, it has been also revealed that when light satisfying $D/S \times \lambda > 1.61$ is used, a favorable measurement result can be obtained even with the subjected eye 100 having the crystalline lens 104 with the opacified portion 105.

The controller 64 is configured to change (adjust) the wavelength swept frequency S of the light outputted from the light source 12 in the present embodiment, however, no limitation is placed thereto. The controller 64 may be configured to adjust the wavelength $\lambda$ of the light outputted from the light source 12, or may be configured to adjust both the wavelength swept frequency S and the wavelength $\lambda$.

Further, the light receiving element 26 and the K-clock generator 60 are connected to the controller 64. An interference signal according to the intensity of interference light detected in the light receiving element 26 is inputted to the controller 64. Further, the K-clock signal generated in the K-clock generator 60 is inputted to the controller 64. The controller 64 samples the interference signal from the light receiving element 26 based on the K-clock signal. That is, the controller 64 functions as an example of "sampling circuit" in the present embodiment. Then, the controller 64 performs Fourier transform on the sampled interference signal to specify the positions of respective parts of the subjected eye 100 (front and rear surfaces of the cornea 102, front and rear surfaces of the crystalline lens 104, front surface of the retina 106) and to calculate an axial length of the subjected eye 100.

Next, a procedure for capturing an optical tomographic image of the subjected eye 100 having the crystalline lens 104 with the opacified portion 105 by using the optical coherence tomographic device of the embodiment will be described. Firstly, an examiner operates an operation member, which is not shown, such as a joystick to position the measurement unit 10 with respect to the subjected eye 100. That is, the controller 64 drives the position adjuster 16 by the first driver 54 in accordance with the examiner's operation to the operation member. Due to this, a position of the measurement unit 10 in xy-directions (vertical-horizontal directions) and a position thereof in a z-direction (a direction in which the measurement unit 10 moves back and forth) are adjusted with respect to the subjected eye 100. Further, the controller 64 drives the second driver 56 to adjust the 0-point adjustment mechanism 30. Due to this, a position of the 0-point at which the object optical path length matches the reference optical path length comes to be positioned at a predetermined position in the subjected eye 100 (for example, at the front surface of the cornea 102).

Next, the controller 64 drives the third driver 58 to adjust the focal adjustment mechanism 40. Due to this, the diameter D of light entering the subjected eye 100 is adjusted. Further, the controller 64 adjusts the wavelength swept frequency S of the light outputted from the light source 12. More specifically, the controller 64 adjusts the diameter D of light and the wavelength swept frequency S such that D/S×λ>1.61 is satisfied. The controller 64 may adjust one of the diameter D of light and the wavelength swept frequency S such that D/S×λ>1.61 is satisfied.

Figure 6:
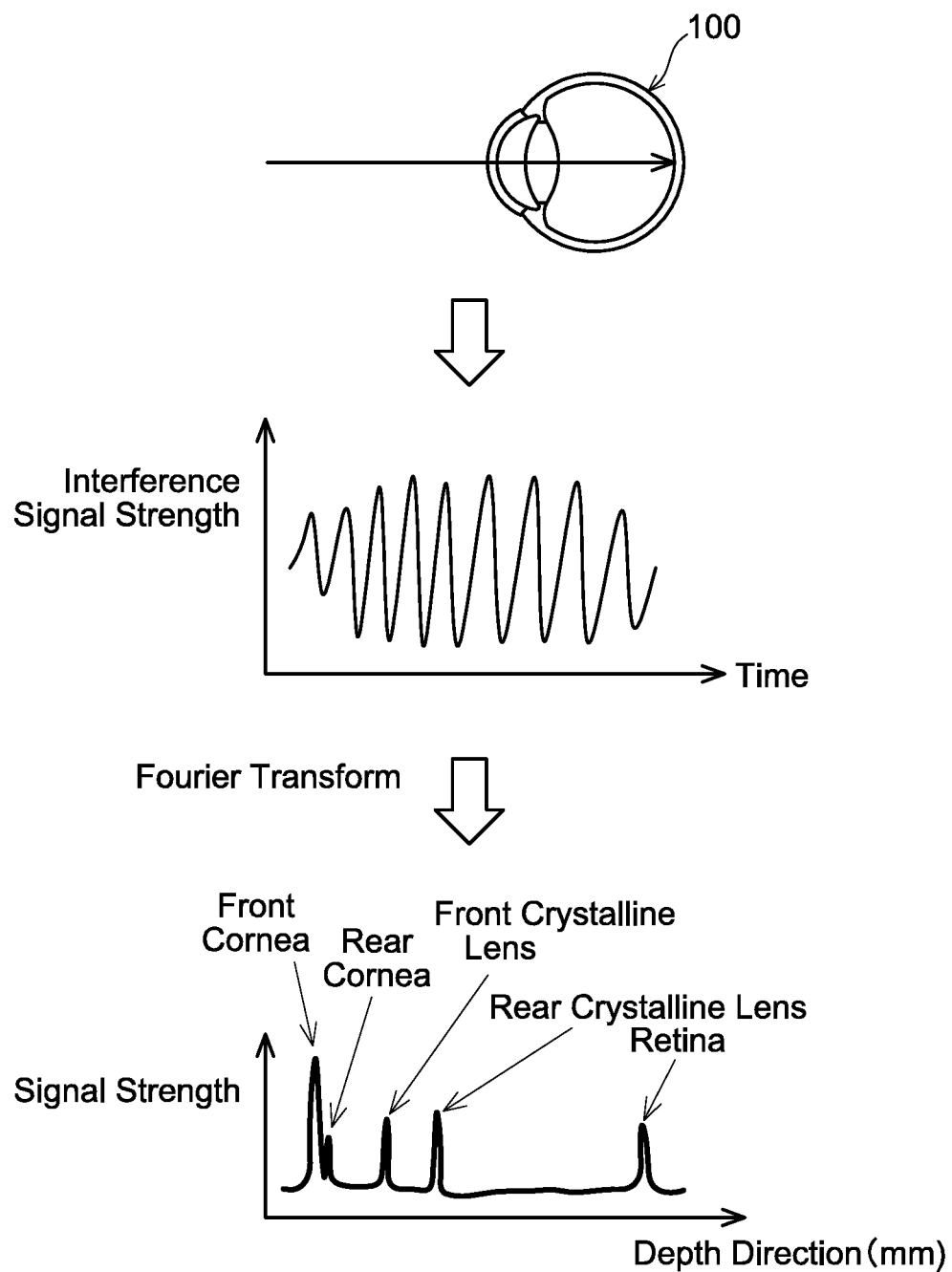
FIG. 6 shows diagrams for explaining a procedure of processing an interference signal waveform.

Then, the controller 64 takes in the signal detected by the light receiving element 26, while changing the frequency of light from the light source 12. As has already been explained, when the frequency of light from the light source 12 changes, the position where the measurement light interferes with the reference light and an interference wave is generated changes in the depth direction of the subjected eye 100. Therefore, the interference signal outputted from the light receiving element 26 becomes a signal of which strength changes with time as shown in FIG. 6, and this signal includes signals created by the interference wave between the reference light and reflected lights from the respective parts (the front and rear surfaces of the cornea 102, the front and rear surfaces of the crystalline lens 104, the surface of the retina 106) of the subjected eye 100. The controller 64 performs the Fourier transform on the signal inputted from the light receiving element 26 to separate, from that signal, interference signal components created by the reflected lights from the respective parts (e.g., the front and rear surfaces of the cornea 102, the front and rear surfaces of the crystalline lens 104, the surface of the retina 106) of the subjected eye 100. Due to this, the controller 64 can specify the positions of the respective parts of the subjected eye 100.

Specific examples of the disclosure herein have been described in detail, however, these are mere exemplary indications and thus do not limit the scope of the claims. The art described in the claims includes modifications and variations of the specific examples presented above. Technical features described in the description and the drawings may technically be useful alone or in various combinations, and are not limited to the combinations as originally claimed.

What is claimed is:

1. An optical coherence tomographic device configured to acquire a tomographic image of a subjected eye, the optical coherence tomographic device comprising:
   a light source of wavelength sweeping type; and
   a measurement optical system configured to irradiate the subjected eye with light outputted from the light source,
   wherein
   D/S×λ>1.61 is satisfied, with a diameter of the light outputted from the light source at an incident position to the subjected eye is D in mm, a wavelength swept frequency of the light source is S in Hz, and a center wavelength of the light outputted from the light source is λ in nm, the diameter D being 3 mm or more, the wavelength swept frequency S ranging from 10 Hz to 5000 Hz.

2. The optical coherence tomographic device according to claim 1, wherein the center wavelength λ ranges from 700 nm to 1400 nm.

3. The optical coherence tomographic device according to claim 1, further comprising a controller configured to control the light source,
   wherein the light source is configured to be capable of adjusting at least one of the wavelength swept frequency S and the center wavelength λ, and
   the controller is configured to adjust at least one of the wavelength swept frequency S and the center wavelength λ of the light outputted from the light source.

4. The optical coherence tomographic device according to claim 1, wherein
   the measurement optical system is configured to be capable of adjusting the diameter D of the light outputted from the light source at the incident position to the subjected eye, and
   the measurement optical system is configured to adjust the diameter D so that the diameter D becomes equal to or less than a pupil diameter of the subjected eye.

5. The optical coherence tomographic device according to claim 4, wherein
   the measurement optical system comprises a focal point adjuster configured to be capable of adjusting a focal position of the light outputted from the light source.

6. The optical coherence tomographic device according to claim 1, further comprising:
   a light receiving element configured to receive reflected light from the subjected eye and to output a signal which corresponds to an intensity of the reflected light;
   a sampling circuit configured to sample the signal outputted from the light receiving element; and
   a sample clock generator configured to generate a clock signal which defines a timing for sampling the signal based on a frequency of the light outputted from the light source.

7. A light source of wavelength sweeping type that is equipped in an optical coherence tomographic device configured to acquire a tomographic image of a subjected eye and is configured to output light with which the subjected eye is irradiated,
   wherein with a diameter of light outputted from the light source at an incident position to the subjected eye is D in mm, a wavelength swept frequency is S in Hz, and a center wavelength is $\lambda$ in nm, the light source is configured to be capable of adjusting at least one of the wavelength swept frequency S and the center wavelength $\lambda$ so that $D/S \times \lambda > 1.61$ is satisfied, the diameter D being 3 mm or more, the wavelength swept frequency S ranging from 10 Hz to 5000 Hz.

* * * * *